(12) United States Patent
Cinelli et al.

(10) Patent No.: US 6,191,189 B1
(45) Date of Patent: *Feb. 20, 2001

(54) ADHESIVE FOR SECURE TOPICAL ATTACHMENT TO THE SKIN AND COMFORTABLE REMOVAL

(75) Inventors: Fabio Cinelli, Bologna; Peter Coles; Italo Corzani, both of Chieti, all of (IT)

(73) Assignee: The Procter & Gamble Company, Cincinnati, OH (US)

( * ) Notice: Under 35 U.S.C. 154(b), the term of this patent shall be extended for 0 days.

This patent is subject to a terminal disclaimer.

(21) Appl. No.: 09/331,741
(22) PCT Filed: Dec. 22, 1997
(86) PCT No.: PCT/US97/23458
  § 371 Date: Jun. 23, 1999
  § 102(e) Date: Jun. 23, 1999
(87) PCT Pub. No.: WO98/27914
  PCT Pub. Date: Jul. 2, 1998

(30) Foreign Application Priority Data

Dec. 23, 1996 (EP) .................................. 96120738
Jul. 1, 1997 (EP) .................................. 97110730
Nov. 20, 1997 (EP) .................................. 97120338

(51) Int. Cl.[7] .................................................... C08L 15/00
(52) U.S. Cl. .................. 523/111; 523/105; 428/355 R
(58) Field of Search ..................... 524/270, 277, 524/322, 481, 505, 578; 525/95; 523/105, 111; 428/343, 355 R, 354

(56) References Cited

U.S. PATENT DOCUMENTS

| | | |
|---|---|---|
| 3,645,835 | 2/1972 | Hodgson . |
| 4,072,151 | 2/1978 | Levine . |
| 4,460,371 | 7/1984 | Abber . |
| 4,593,053 * | 6/1986 | Jevne et al. ............................ 523/11 |
| 4,699,146 * | 10/1987 | Sieverding ............................ 128/640 |
| 5,418,052 * | 5/1995 | Sugie et al. ............................ 428/261 |
| 5,559,165 * | 9/1996 | Paul ...................................... 523/111 |
| 5,658,270 | 8/1997 | Lichstein . |

FOREIGN PATENT DOCUMENTS

| | | |
|---|---|---|
| 0 184 470 | 6/1986 | (EP) . |
| 0 730 874 | 9/1996 | (EP) . |
| 0 510 200 | 7/1999 | (EP) . |
| 2 115 431 | 9/1983 | (GB) . |
| 2 183 174 | 6/1987 | (GB) . |
| 2 284 767 | 6/1995 | (GB) . |
| WO 93/10201 | 5/1993 | (WO) . |
| 16424 * | 6/1995 | (WO) ...................................... 13/58 |
| WO 96/29968 | 2/1996 | (WO) . |
| WO 96/13238 | 5/1996 | (WO) . |
| WO 98/23305 | 11/1996 | (WO) . |
| WO 98/28203 | 12/1996 | (WO) . |
| WO 99/15123 | 9/1998 | (WO) . |

* cited by examiner

Primary Examiner—Edward J. Cain
Assistant Examiner—Katarzyna Wyrozebski
(74) Attorney, Agent, or Firm—Leonard W. Lewis; Jerry Yetter; Matthew P. Fitzpatrick

(57) ABSTRACT

The present invention relates to a combination of a substrate with topical adhesives for attachment to the skin. In particular the present invention relates to a combination of a substrate with a topical adhesive which can be employed for attachment to the skin in the area where absorption of bodily liquids is desired. The combination provides secure attachment and is pleasing to the skin upon application, yet causes no discomfort upon removal. This is achieved by selecting the chemical composition and rheological characteristics of the topical adhesives and the physical characteristics of the substrate on which the topical adhesive is applied.

10 Claims, No Drawings

ADHESIVE FOR SECURE TOPICAL ATTACHMENT TO THE SKIN AND COMFORTABLE REMOVAL

FIELD OF THE INVENTION

The present invention relates to a combination of a substrate with a topical adhesive for attachment to the skin. In particular the present invention relates to a combination of a substrate with a topical adhesive which can be employed for attachment to the skin in the area were absorption of bodily liquids is desired, particularly for the adhesion of sanitary napkins, pantiliners, adult incontinence products or sweat pads. The combination provides secure attachment and is pleasing to the skin upon application, yet causes no discomfort upon removal. This is achieved by selecting the chemical composition and rheological characteristics of the topical adhesives and with the physical characteristics of the substrate on which the topical adhesive is applied, particularly the viscous modulus G" of the topical adhesive and the stiffness S of the combination of the substrate with the topical adhesive.

BACKGROUND OF THE INVENTION

The general prior art in the field of topical adhesives for attachment to the skin is particularly developed in the field of band-aids, plasters and bandages. These articles are, however, typically applied in an emergency situation where for example a cut into the skin of the wearer has occurred and absorption of the body liquids emanating from a wound is desired. In this context performance aspects of the absorbent article such as comfortable and easy use and application, painless removal, discreteness are subordinate to criteria such as sterility, healing support, mechanical protection of the wound. Also such wound covering absorbent articles are mostly adhered to skin areas where prior to application of the absorbent article body hair can be removed or where little or no hair grows.

The present invention relates to combination of a substrate with a topical adhesive which is particularly useful to absorbent articles for absorption of body liquids which naturally emanate from a body without a wound. For example to attach sanitary napkins or pantiliners in the genital region. Also incontinence devices which are worn e.g. in the genital region or sweat pads which are worn in the arm pit region of a person can suitably employ the adhesive of the present invention.

Topical adhesives that are used for absorbent articles have generally been disclosed in US statutory invention registration H1602 or WO 96/33683. Some more details of the adhesive have been disclosed in PCT application WO 95/16424. In this document sanitary articles having a topical adhesive which is applied on the wearer facing side of a sanitary napkin along the entire periphery are disclosed. The problem underlying this document is primarily the safe attachment to the skin but mentions also the problems of detachment of such articles after use without causing undue pain to a wearer.

The disclosure of WO 95/16424 includes a detailed analysis of the criteria for the topical adhesive in respect to rheological criteria. However, this document has little regard to the problem of painless removal of such articles since the rheological criteria taught include epilatory, i.e. hair removal, compositions which are commercially available such as STREP MIELE™ sold in Italy by Laboratori Vaj S.p.A. The adhesives for topical attachment mentioned in WO 95/16424 include also today's pressure sensitive adhesives which are used to attach sanitary napkins to undergarments. Further, this document only identifies static rheological characteristics but is silent as to the dynamic rheological behaviour of a topical adhesive.

In WO 96/13238 a frequency dependent topical adhesive model is disclosed. However, all measurements disclosed, e.g. on page 9, were made at temperatures between −60° C. and +120° C. and at actual frequencies of 0.1 to 100 rad/s. In order to obtain the necessary data at application temperature (about 20° C., typical bath room, i.e. storage temperature) the Williams-Landel-Ferry (hereinafter WLF) equation was used.

This WLF equation is empirical and only valid within certain limits e.g. it cannot be used to extrapolate to temperatures below the glass transition temperature of a polymeric adhesive also the WLF cannot be used on the basis of values obtained below the glass transition temperature. Details about the WLF equation and its applicability can be found in "Principles of Polymer processing" by Z. Tadmor and C. G. Gogos, published by John Wiley & Sons or in "Viscoelastic Properties of Polymers" by J. D. Ferry also published by John Wiley & Son. Since this is already missing from WO 96/13238 the applicability of the disclosed data cannot be assessed.

European Patent Application EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth. Both applications are silent as to the adhesive composition.

Based on the above state of the art it is an objective of the present invention to provide a combination of a substrate with a topical adhesive for secure attachment and painless removal from the skin of a disposable absorbent article. It is another objective of the present invention to ensure upon removal that no residual adhesive remains on the skin or on the hair.

It is yet a further objective of the present invention that the adhesive of the combination for topical attachment does not cause a cold or otherwise unacceptable temperature sensation upon application despite a temperature difference of the adhesive in respect to the skin temperature.

In addition to the above objectives of the present invention it is also desirable for topical adhesives of the combination to provide additional benefits such as delivery/dispersal of a compound or composition which is beneficial for the skin or for the body in general. Further, topical adhesives which do not affect the natural skin condition, e.g. by being breathable or water vapour transmitting or water vapour/sweat absorbing, are preferred.

BRIEF DESCRIPTION OF THE INVENTION

The present invention will be explain ed in its use on disposable absorbent articles for topical adhesive attachment to a wearer of such articles. The article typically has a wearer or body facing surface and an outside surface. The article comprises an absorbent core structure between the wearer facing surface and the outside surface for absorbing liquids emanating from a wearer such as urine, feces, menses, sweat and vaginal discharge. The article further comprises a combination of a substrate with a topical adhesive applied thereon, the combination having a stiffness or flexibility S measured in grams (g) according to the Flexibility Test method described hereinafter. The topical adhesive of the combination allows to attach an article to the skin of the wearer, being typically applied on the substrate on at least part of the wearer facing surface of the article.

Detailed analysis of the sequence of common situations occurring from the application of a disposable absorbent article to the time of removal of such an article has shown that specific adhesive characteristics need to be preferably satisfied in order to achieve the desired performance objectives, in particular secure initial attachment, secure attachment during use and painless removal at the end. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere. The elastic behaviour can be interpreted as an indication of the "hardness" behaviour of the adhesive. Its value is also critical for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide the combination of the present invention of a substrate with a topical adhesive for secure initial and prolonged attachment and easy/painless removal the relation between the elastic modulus and the viscous modulus as well as their dynamic behaviour is of key importance.

The topical adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$. The adhesive further has a dynamic elastic behaviour defined as $\Delta G'_{37}$ which is the difference of $G'_{37}$ at a frequency of 100 rad/sec and $G'_{37}$ at a frequency of 1 rad/sec and a dynamic viscous behaviour $\Delta G''_{37}$ which is the difference of $G''_{37}$ at a frequency of 100 rad/sec and $G''_{37}$ at a frequency of 1 rad/sec.

The topical adhesive according to the present invention preferably satisfies the following conditions.

$G'_{37}$ (1 rad/sec) is in the range 1500 Pa to 20000 Pa, preferably 1500 Pa to 15000 Pa, most preferably 3000 Pa to 10000 Pa.

$G''_{37}$ (1 rad/sec) is in the range 100 Pa to 15000 Pa, preferably 100 Pa to 10000 Pa, most preferably 300 Pa to 5000 Pa.

the ratio of $G'_{37}$ (1 rad/sec) /$G''_{37}$ (1 rad/sec) is in the range of 3 to 30.

the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

is not less than 0.5, preferably in the range 0.7 to 3, most preferably in the range 1 to 1.8.

either the ratio of $\Delta G'_{37}/G'_{37}$ (1 rad/sec) is not greater than 1.5, preferably not greater than unity and most preferably not greater than 0.8, or $\Delta G'_{37}$ is not greater than 10000 Pa, preferably less than 5000 Pa, most preferably less than 2000 Pa, or both.

the value of the ratio $G'_{37}/G''_{37}$ at least for the frequency range from above 1 rad/s up to 100 rad/s should preferably be 3.3 or above, more preferably 5 or above, most preferably 10 or above, while not exceeding about 30, preferably 20, anywhere in the frequency interval.

the rheological behaviour can also be related to the values of the Glass Transition Temperature Tg. For topical adhesives according to the present invention Tg should preferably be less than −15° C., more preferably less than −20° C. and most preferably less than −25° C.

the rheological behaviour and acceptance of a topical adhesive can also be related to the specific heat capacity. Preferably the specific heat capacity of the topical adhesive is less than 4 J/g/K, more preferably less than 3 J/g/K and most preferably less than 2 J/g/K.

the rheological behaviour and acceptance of a topical adhesive can also be related to the specific heat conductivity of the adhesive. Preferably the specific heat conductivity is as low as possible, preferably between 1 and 0.1 W/m/K, most preferably between 0.6 and 0.1 W/m/K.

Provided the above rheological conditions are satisfied the adhesives will also satisfy conditions such as sufficient cohesiveness (to prevent residue of adhesive on skin) which are critical for commercial use of such adhesives and apparent to those skilled in the art. Adhesive compositions which satisfy the above criteria can be used as topical adhesives for disposable absorbent articles provided they also satisfy the common requirements of being safe for use on human or animal skin during use and generally after disposal of the article.

Often the criteria of hygienic appearance and pleasant feel upon contact are important such that adhesive composition which are transparent or white, and which prevent a cold, unpleasant feeling upon application are preferred.

The above rheological criteria and other considerations can be satisfied by adhesive compositions where the composition comprises from 45%, preferably from 51%, to 99.5% of a plasticising compound or composition which is liquid at 20° C., from 0.5 to 20%, preferably 5% to 15%, of a polymeric compound or composition which is soluble or swellable in the plasticising compound or composition and with a tackifying resin in an amount in the range from 0% to 50% by weight of the composition, preferably from 0% to 600% by weight of the polymeric compound. The plasticising compound or composition is preferably selected from the group consisting of water, alcohols (preferably glycerol), glycols, polyglycols, liquid polybutenes, oil or combinations thereof. The polymeric compound or composition is preferably selected from the group consisting of block-copolymer-thermoplastic-elastomers, styrene-block-copolymers and hydrogenated styrene-block-copolymers, polyacrylics, polyvinyl alcohol, natural gum or gelatines, polyethyleneoxide, polyvinylpyrrolidon (PVP), polyvinylethers, cellulose derivatives, or combinations thereof.

According to the present invention, it has been discovered that the relation between the stiffness or flexibility S of the combination of the substrate with the topical adhesive applied thereon, on at least part of the body facing surface of the disposable absorbent article, and the viscous modulus $G''_{25}$ at about 100 rad/sec of the topical adhesive is relevant to the scope of providing an easy and painless removal from the wearer's skin of such a combination of a substrate with a topical adhesive used for attachment of a disposable absorbent article to the skin of a wearer.

The combination according to the present invention of the substrate with the topical adhesive applied thereon is such that the viscous modulus $G''_{25}$ (100 rad/sec) of the topical adhesive and the stiffness or flexibility S of the combination satisfy the following empirical equation:

$$G''_{25} \leq [(163.8 + S) \cdot 50.9] Pa$$

and preferably the following empirical equation:

$$G''_{25} \leq [(82.2 + S) \cdot 51.4] Pa$$

DETAILED DESCRIPTION OF THE INVENTION

Adhesive for Topical Attachment

The topical adhesive of the combination of the present invention is applied directly to the skin. In a particular application the adhesive can be used on sanitary napkins which are applied in the genital region of a typically female user around the area of liquid discharge. The word "skin" according to the present invention does not only relate to the specific derma of the user but includes the mucous tissue as well as the hair which is typically found in the genital region of users of sanitary napkins.

In order to provide fixation of an article to the skin it is generally necessary to provide a certain area on the side of the article which is facing the skin with the topical adhesive.

Typically the topical adhesive of the combination of the present invention is provided onto at least part of the wearer facing surface of the disposable absorbent article by being applied on a substrate, which combination has a stiffness S measured in grams (g) according to the Flexibility Test described hereinafter. The combination can be joined or affixed with any known means to the disposable absorbent article as an additional layer, constituting at least part of the body facing surface of the article or, preferably, the combination can comprise partially or totally the absorbent article itself. For example, the substrate can be the topsheet of the absorbent article, or, alternatively, the substrate can be the entire absorbent article.

As far as the evaluation of the stiffness S of the combination is concerned, as will be explained in more details hereinafter, it can be assumed that in most cases the stiffness of the combination actually corresponds to the stiffness of the entire absorbent article including the topical adhesive, in the preferred embodiment when the substrate actually corresponds to the entire absorbent article. Therefore it can be said that preferably the substrate actually comprises the entire disposable absorbent article, typically constituted by at least a liquid pervious topsheet, a liquid impervious backsheet joined to said topsheet, and an absorbent core positioned between said topsheet and said backsheet.

For sanitary napkins various designs are contemplated but preferably the topical adhesive is provided along the peripheral edge of the topsheet such that a central area of the article is left without adhesive. This will most appropriately facilitate placing the napkin such that the liquid permeable topsheet region without adhesive is placed adjacent the bodily liquid emanating orifice such that emanating liquid is immediately transported into the absorbent structure of the absorbent article without the possibility of leakage or spillage.

The topical adhesive is provided with the preferred pattern on the substrate on the wearer facing surface of the article in a layer that can be preferably continuous or alternatively discontinuous, e.g. in form of dots, spirals, or stripes, and having a thickness or caliper that is preferably constant.

Physical, Rheological and Adhesive Characteristics of a Topical Adhesive

Even though topical adhesives are used like pressure sensitive adhesives on human skin hair and mucous tissues, it is understood that the topical adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily stick things (as e.g. water between two glass plates could) is the fact that their rheological parameters and especially the Elastic Modulus G' vary greatly with the frequency of applied stresses. More in particular, G' of PSA can increase over some orders of magnitude while the frequency of applied stresses varies from typical bonding frequency to typical debonding frequency, i.e. 1 rad/s to 100 rad/s as indicated below.

As a first consequence, it derives that it is inadmissible to define materials intended for use as "topical adhesives" by giving values of rheological parameters and especially of G' at a fixed value of frequency. This can be misleading because in the absence of other characteristics it will include materials which have no practical value. It is hence necessary that rheological characterisation must be on the base of dynamic considerations.

This not only applies to the Elastic Modulus G' but also to the viscous modulus G" and hence also for tan $(\delta) = G''/G'$. It is well known that typical PSA have not only a high variation of G' across the considered frequencies but also there is an even higher variation of G" which can get close or become even higher than the value of G', i.e. tan $(\delta)$ becomes about or even greater than 1, in particular at the frequencies that are typical of the debonding.

Without wishing to be bound by theory this can be interpreted as meaning that a high fraction of the energy applied for the debonding is dissipated within the adhesive (so it is not effective in causing the debonding) while this fact causes macroscopically the recording of a very high level of adhesive force.

As indicated above materials useful as topical adhesives according to the present invention have rheological characteristics which are mostly measured at a reference temperature of 37° C. (as usual body temperature of humans) and in a range of frequencies. It has been found that upon application of an article such as a sanitary napkin with a topical adhesive the adhesive contact is formed at a low frequency, while debonding happens at the speed of removing the article. This speed is expressed as a frequency of 100 rad/s while the low frequency of forming the adhesive bond has been found to be on the order of 1 rad/s. Therefore, the frequency range for use according to the present invention is between 1 and 100 rad/s.

It is believed that the adhesive bonding characteristics are selected most appropriately at human body temperature. Since the topical adhesive according to the present invention is used directly on skin and the person skilled in the art is directed to select the adhesive composition to have a small specific heat capacity (e.g. preferably less than 4 J/g/K) the actual temperature of the topical adhesive will reach 37° C. very quickly or even be warmed up by a human prior to application.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion which is particularly valuable for use in the field of sanitary napkins while the material remains soft and capable of gently adhering to skin.

The ratio of $G'_{37}$ (1 rad/sec) over $G''_{37}$ (1 rad/sec) is important to ensure that these two values are balanced upon adhesion to the skin. At the same time the absolute changes of $G'_{37}$ need to be limited within the range of frequencies considered. Hence a value for the ratio of $\Delta G'_{37}$ (i.e. $G'_{37}$ (100 rad/sec)-$G'_{37}$ (1 rad/sec)) over $G'_{37}$ (1 rad/sec) has to be kept small in order to maintain the secure attachment of the topical adhesive without causing discomfort over time or at removal/ delamination. This can also be expressed in absolute terms by keeping the $\Delta G'_{37}$ below certain values.

Importantly, the ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, specific heat capacity, and specific heat conductivity are parameters which are useful to more fully define the group of useful topical adhesives.

The following set of characteristics should be preferably satisfied for the topical adhesive of the combination of the present invention:

$G'_{37}$ (1 rad/sec) is in the range 1500 Pa to 20000 Pa, preferably 1500 Pa to 15000 Pa, most preferably 3000 Pa to 10000 Pa.

$G''_{37}$ (1 rad/sec) is in the range 100 Pa to 15000 Pa, preferably 100 Pa to 10000 Pa, most preferably 300 Pa to 5000 Pa.

the ratio of $G'_{37}$ (1 rad/sec)/$G''_{37}$ (1 rad/sec) is in the range of 3 to 30.

the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

is not less than 0.5, preferably in the range 0.7 to 3, most preferably in the range 1 to 1.8.

either the ratio of $\Delta G'_{37}/G'_{37}$ (1 rad/sec) is not greater than 1.5,
preferably not greater than unity and most preferably not greater than 0.8,
or $\Delta G'_{37}$ is not greater than 10000 Pa, preferably less than 5000 Pa, most preferably less than 2000 Pa,
or both.

the value of the ratio $G'_{37}/G''_{37}$ at least for the frequency range from above 1 rad/s up to 100 rad/s should preferably be 3.3 or above, more preferably 5 or above, most preferably 10 or above, while not exceeding about 30, preferably 20, anywhere in the frequency interval.

the rheological behaviour can also be related to the values of the Glass Transition Temperature Tg. For topical adhesives according to the present invention Tg should preferably be less than −15° C., more preferably less than −30 20° C. and most preferably less than −25° C.

the rheological behaviour and acceptance of a topical adhesive can also be related to the specific heat capacity. Preferably the specific heat capacity of the topical adhesive is less than 4 J/g/K, more preferably less than 3 J/g/K and most preferably less than 2 J/g/K.

the rheological behaviour and acceptance of a topical adhesive can also be related to the specific heat conductivity of the adhesive. Preferably the specific heat conductivity is as low as possible, more preferable between 1 and 0.1 W/m/K, most preferably between 0.6 and 0.1 W/m/K.

Chemical and Compositional Characteristics of a Topical Adhesive

In order to provide topical adhesive compositions which satisfy the requirements of the above Theological and physical characteristics of a topical adhesive the following formulation criteria can be used in addition. It should be noted that the most of the compositions useful as topical adhesive have a substantially gel-like structure and are preferably gels. This derives from the fact that:

the prevailing component is the plasticiser which is a material liquid at room temperature a macromolecular or polymeric component is present in minor quantities vs. the plasticiser. It forms, in the preferred embodiments, a three dimensional network caused by physical or chemical links between the molecules. Particularly useful physical links are the ones present in systems containing Block Thermoplastic Elastomers.

More specifically, the compositions typically comprise:

from 0.5 to 20%, preferably 5% to 15%, by weight of a macromolecular polymeric substance or a mixture of such substances soluble or swellable in the below mentioned plasticiser(s). As not limiting examples such macromolecular or polymeric substances can be natural and/or synthetic such as natural gums or derivatives such as natural gums and gelatins, their derivatives and alginates; polyacrilics; polyvinyl alcohol; polyethylene oxide; polyvinylpyrrolidon (PVP) or polyvinylethers, their copolymers and derivatives; cellulose derivatives; Block Copolymer Thermoplastic Elastomers and preferably Styrenic Block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS).

from 45 to 99.5% by weight, preferably from 51 to 99.5% by weight, of a plasticising substance or a mixture of plasticising substances, which are liquid at room temperature. As non-limiting examples the plasticiser can be water, various alcohols (like in particular glycerol), glycols and their ethers, polyglycols, liquid polybutenes, esters such phthalates, adipates, stearates, palmitates, sebacates, or myristates, natural or synthetic oils such as vegetable oils, mineral oils, or combinations thereof.

from 0% to 50% by weight of the composition, preferably from 0 to 600% by weight of the macromolecular polymeric substance of a tackifying resin whose main scope is to tailor the Tg especially in systems based on synthetic polymers.

from 0 to 10% and more preferably form 0 to 5% by weight of substances for facilitating and stabilising the gel and the gel forming process both of hydrophilic or hydrophobic liquid plasticisers. These may be for oily systems, e.g. the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservatives, antioxidants, anti UV, pigments, mineral fillers, rheology modifiers etc. can also be comprised in quantities up to 10% each.

When chemical crosslinks are formed in the system, a crosslinking agent can be present preferably in quantities up to 5% by weight. Chemical crosslinking can be formed also by mutual neutralisation of polymers having different functionalities as in the reaction between acid polyacrylics and polysaccharides.

The resulting compositions for topical adhesives can be divided into three families according to the nature of the main component, i.e. usually the liquid plasticiser(s):

1) Hydrophobic compositions in which the plasticiser is typically an oil or blend of oils of vegetable or mineral origin and the polymer is usually a synthetic polymer, preferably an elastomer, soluble or swellable in oil(s).

2) Mixed phase compositions in which both hydrophobic and hydrophilic components, possibly in both plasticisers and polymers, form two or more separate phases. In such cases an emulsifier/surfactant is preferably present at a suitable level to form stable emulsions between the incompatible phases. For topical adhesives according to the present invention it is preferably that the hydrophobic components are prevailing vs. the hydrophilic ones.

3) Hydrophilic compositions in which typically the plasticiser is water/glycerol/glycols and the like and/or mixtures thereof and the polymeric phase is of synthetic (e.g. polyacrilics) or natural (e.g. natural gums) origin or mixtures thereof.

It is to stress that, differently from the medical field and from the cited prior art, the hydrophilic compositions are not preferred while the hydrophobic and mixed phases compositions 1) and 2) are preferred in the applications of the present invention.

This depends partially on technical reasons in the sense that many hydrophilic compositions used in the medical field show too low elastic character and cohesion for being useful in the present application. The other reason to prefer hydrophobic or mixed phase compositions is that the application of the present invention in particular in the sanitary napkin field will include a probability of contacting the topical adhesive with the liquid to be absorbed. Since the liquids are all of a general aqueous kind contact with a hydrophilic topical adhesive would result in a certain absorption of the bodily liquids into the topical adhesives.

This would then have the result of changing the rheological characteristics and therefore the functionality of the topical adhesive and causing a non-hygienic appearance.

Further hydrophilic topical adhesives also tend to be perceived as cold and wet which upon application to the skin of a human is not in line with typical expectation. Additional problems result from the fact that in particular topical adhesives comprising water as the plasticiser have a tendency to dry out unless they are sealed into an impermeable package.

Application of Topical Adhesive

Absorbent articles in which the combination according to the present invention comprising the topical adhesive can be used, can be made by any of the ways usual in the art. The application of the adhesive to a substrate to form the combination of the present invention should not cause major problems to those skilled in the art since it can be provided by any well known techniques commonly used for other adhesives.

As already mentioned, the combination of the substrate with the topical adhesive can be applied to the absorbent article as an additional layer. Alternatively, and preferably, the substrate can be partially or totally the absorbent article itself. For example, the substrate of the combination can be the topsheet of the absorbent article. Preferably, the substrate of the combination of the present invention is the entire disposable absorbent article.

The substrate can comprise any suitable material, provided that the conditions set forth hereinbelow are satisfied. In the embodiment where the substrate is actually the topsheet of the absorbent article, any material commonly used as a topsheet is suitable as the substrate for the topical adhesive composition in order to form the combination according to the present invention. In most cases the substrate of the combination according to the present invention is the entire absorbent article, e.g. comprising at least a topsheet, a backsheet and an absorbent core therebetween.

Overall, the total area of the skin or wearer facing surface of an absorbent article comprising the combination of the present invention which is covered by the topical adhesive should be not more than 20%, preferably not more than 10%. Preferably, the adhesive is close to the periphery of the absorbent article and when the substrate of the combination is constituted by, or comprises a film topsheet, the adhesive can be preferably on a portion of the film which is not permeable to liquids.

The topical adhesive is applied on the substrate to form the combination on at least part of the wearer facing surface of the disposable absorbent article in a layer having a thickness or caliper that is preferably constant, or that alternatively can vary over the surface interested by the application of the topical adhesive.

If possible, the article also provides breathability by being at least water vapour permeable, preferably air permeable to prevent stuffiness. Breathability, if not supported by the topical adhesive as such, can be limited to the area of the article where no adhesive is applied.

The topical adhesive on an article is preferably protected prior to use. This protection can be provided by a release liner such as a siliconised or surfactant treated paper, providing easy release for the selected topical adhesive.

This invention can be used beneficially on disposable absorbent articles which are applied directly to the skin of a user. The article usually exhibits absorbency for bodily fluids, the protection of the user's garments from soiling, is comfortable to the user, and is easy to produce and to package. The disposable absorbent article is described below by reference to a sanitary napkin or catamenial, however panty liners, adult incontinence articles or sweat pads are also included under the term disposable absorbent articles. The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use. A disposable absorbent article is preferably thin, more preferably between 1 and 5 mm thick and either substantially flat prior to use or in a preshaped form.

The terms "joined" or "affixed", as used herein, encompasses configurations whereby a first member is directly connected to a second member and configurations whereby a first member is indirectly connected to a second member by connecting the first member to intermediate members which in turn are connected to the second member.

In a preferred embodiment a sanitary napkin of the present invention comprises a liquid pervious topsheet, a liquid impervious backsheet joined to the topsheet, and an absorbent core intermediate the topsheet and the backsheet. The sanitary napkin has two main surfaces, a body contacting or wearer facing surface on which the topical adhesive is applied and a garment facing or contacting surface.

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

In order to form a preferred combination of a substrate with the topical adhesive said topical adhesives are most suitably applied on topsheets having not a homogeneous distribution of liquid passage ways but only a portion of the topsheet comprising liquid passage ways oriented such that they result in a centrally permeable and peripherally impermeable topsheet for liquids.

Another alternative are so called hybrid topsheets which incorporate fibrous and film like structures particularly useful embodiments of such hybrid topsheets are disclosed in PCT publications WO 93/09744; WO 93/11725 or WO 93/11726.

When referring to the topsheet a multi layer structure or a mono layer structure is contemplated. The hybrid topsheet mentioned above is such a multi layer design but other multi layer topsheets such as primary and secondary topsheet designs are also considered.

The absorbent core also can comprise multiple layers and provides fluid storage and distribution function.

Positioned in fluid communication with, and typically underlying the topsheet is the absorbent core. The core can comprise any usual absorbent material or combinations thereof. It preferably comprises absorbent gelling materials usually referred to as "hydrogel", "superabsorbent", "hydrocolloid" materials in combination with suitable carriers.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared form polymerizable, unsaturated, acid-containing monomers, such as acrylic acid, which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the core, particularly useful in the application of the present invention, comprises a double layer tissue laminate formed by folding the tissue onto itself. These layers can be joined to each other. Absorbent gelling material or other optional material can be comprised between the layers.

The absorbent core can include optional components normally present in absorbent webs such as odor control agents, in particular suitable zeolites.

The backsheet primarily prevents the exudates absorbed and contained in the absorbent core from wetting articles that contact the absorbent product such as underpants, pants, pyjamas and undergarments. The backsheet is preferably impervious to liquids (e.g. menses and/or urine) and usually manufactured from a thin plastic film.

The backsheet typically extends across the whole of the absorbent core and can extend onto and form part of the topsheet by folding around the absorbent core. Thereby a topsheet configuration as disclosed in U.S. Pat. No. 4,342,314, column 16, lines 47–62 can be achieved without the requirement to selectively aperture the topsheet.

Preferably, the backsheet also provides breathability to the absorbent article by being at least water vapour permeable, preferably air permeable. The backsheet can be a laminate material e.g. of a combination of microporous film and/or non-woven material, and/or apertured formed film. Breathability if desired can be limited to the periphery or the center of the backsheet or it can be across the whole backsheet.

When considering particularly the removal phase of a combination of a substrate with a topical adhesive composition for attachment of disposable absorbent articles to the skin of a wearer, it is commonly recognized that good conditions of removal, i.e. at a frequency of about 100 rad/sec, of the topical adhesive applied to at least part of the wearer facing surface of a disposable absorbent article for attachment of said article to the skin of a wearer, are achieved when the adhesive can be easily removed from the skin, and particularly from the hairs that typically grow on it where the disposable absorbent article contacts the body, without causing pain to the wearer, therefore without sticking too hard upon removal to the skin and hairs of the wearer. Moreover, a good removal implies that the topical adhesive does not leave residual remains on the skin or on the hairs.

According to the present invention, the relationship between the stiffness or flexibility S of the combination of the substrate with the topical adhesive applied thereon, as measured in grams according to the Stiffness Test described hereinbelow, and the viscous modulus $G''_{25}$ at 25° C. and about 100 rad/sec of the topical adhesive gives an indication on the painless and easy removal of the topical adhesive from the wearer's skin.

It has been discovered that for higher values of the viscous modulus $G''_{25}$ at 100 rad/sec, which overall correspond to a higher adhesiveness of the composition, a higher stiffness S of the combination of the substrate with the topical adhesive is needed, in order to reduce the pain sensation to the wearer when the absorbent article comprising the combination is removed from the skin. In other words, less stiff combinations of substrates with topical adhesives necessitate an adhesive with a lower $G''_{25}$ at 100 rad/sec to achieve a reduced pain sensation upon removal of the absorbent article comprising the combination.

According to the present invention, the combination of the substrate with the topical adhesive applied thereon, said combination having a stiffness S, is such that the viscous modulus $G''_{25}$ (100 rad/sec) and the stiffness or flexibility S satisfy the following empirical equation:

$$G''_{25} \leq [(163.8+S) \cdot 50.9] \text{Pa}$$

and preferably the following empirical equation:

$$G''_{25} \leq [(82.2+S).51.4] Pa$$

The stiffness or flexibility S of the combination of the substrate with the topical adhesive is measured in grams (g) according to the Stiffness Test. It depends on the nature of the substrate and adhesive.

In accordance with the present invention the substrate comprises all layers that are joined to each other so as to unify them at least in the region corresponding to the region occupied by the topical adhesive. The stiffness of the combination of substrate plus topical adhesive depends strongly on which materials and how many layers actually correspond to the substrate.

As already mentioned, the combination of the substrate with the topical adhesive can be joined or affixed to the disposable absorbent article, or alternatively, the substrate can comprise partially or totally the absorbent article.

The substrate of the combination can be joined or affixed to the absorbent article by any known means, e.g. by adhesive bonding, thermal bonding, mechanical bonding, or any combination thereof, but outside the region corresponding to the region where the topical adhesive is applied.

In such an embodiment of the present invention the substrate of the combination can comprise one or more separate layers joined or affixed to the absorbent article e.g. along their respective contour edge, the remaining portions of the substrate being not joined to the absorbent article. In this case the stiffness of the combination which is relevant in the removal of the absorbent article is that of the layer or layers constituting the substrate.

If the substrate comprises partially the absorbent article, e.g. typically corresponding to the topsheet, it can only be joined or affixed to the remaining part of the absorbent article substantially outside the region corresponding to the region occupied by the topical adhesive. Outside this region the substrate is joined by any known means.

In most cases the flexibility or stiffness of the combination of the substrate with the topical adhesive actually corresponds to the flexibility or stiffness of the entire absorbent article including the topical adhesive, when the layers of the entire article are joined to each other so as to unify them at least in the region corresponding to the region occupied by the topical adhesive.

In order to evaluate the effect of the stiffness S of the combination of the substrate with the topical adhesive in its relationship with the viscous modulus $G''_{25}$ (100 rad/sec) of the topical adhesive used for the attachment of a disposable absorbent article to the skin of a wearer, a Removal Pain Grade Test has been developed where the adhesion of combinations having different stiffnesses due to different substrates covered with a layer of the same topical adhesive, on the skin of the forearm of members of a sensory panel is achieved, and upon successive removal the pain is evaluated in terms of pain grades.

The stiffness of the combinations is in turn evaluated according to the Stiffness Test described hereafter.

TEST METHODS

Removal Pain Grade Test

The Removal Pain Grade Test is utilized to evaluate the pain during removal from the skin of a wearer of a sample provided with a layer of a topical adhesive and previously attached to the wearer's skin. The test specifically evaluates the pain upon removal of each sample as compared to the pain obtained by removing a reference sample constituted by a commercial strong medical plaster.

Sample Preparation.

The test is performed on rectangular samples 60×20 mm of the selected substrate provided on one side with a continuous layer of the topical adhesive having a constant thickness, applied with an Acumeter Model LH-1 extruder. The samples represent the different combinations of substrates with the topical adhesive. The reference sample is a 60×20 mm sample of a medical double sided adhesive tape produced by Minnesota Mining and Manufacturing Company under the trade name of No. 1524 Medical Tape; only one of the two layers of adhesive is exposed on the reference sample and used for attachment to the skin during the test.

Test Method.

A panel of six graders is selected for the test. The test is performed in a climatically controlled lab where a temperature of 23° C. and a Relative Humidity of 50% are maintained. No special treatment of the wearer's skin is required beyond normal cleaning/washing with water and soap and drying at least two hours before the test to allow equilibrium with the room conditions is reached for the skin. Three different samples A, B, and C are evaluated in the test in comparison with the reference sample R. Each sample is applied by hand by an operator to the inner part of the grader's forearm, being centered between the wrist and the elbow, with the short side of the sample aligned with the length of the arm. The operator exerts on each sample with his palm the same pressure that is typically applied to cause a medical plaster to adhere to the skin. Each sample is worn for the prescribed time, and then it is removed from the grader's skin by the operator with a slow and smooth pull.

Four series of one reference sample R and three samples A, B, and C each are applied, worn and then removed from the wearer's skin; each sample is worn for one minute, with a 5 minute wait between two subsequent samples of the same series, and a 15 minute wait between two different subsequent series. The reference sample R is always applied, worn and removed as the first sample of its respective series. The sequence of application/wear/removal of A, B, C samples in each of the first three series is random, provided that no repetition in each series is allowed, and that no sequence is repeated in the first three series. In the fourth series of four samples one of A, B, or C samples is tested twice, the reference R always being the first one.

Overall each sample (A, B, C, and R) has to be tested an equal number of times (24 times according to the scheme below).

In the performed tests the sequences of the four series are according to the following scheme:

| Grader | 1st series | 2nd series | 3rd series | 4th series |
|--------|-----------|-----------|-----------|-----------|
| 1 | RABC | RCAB | RBCA | RAAB |
| 2 | RCAB | RBCA | RABC | RBCC |
| 3 | RBCA | RABC | RCAB | RCAA |
| 4 | RABC | RCAB | RBCA | RBBC |
| 5 | RCAB | RBCA | RABC | RAAB |
| 6 | RBCA | RABC | RCAB | RBCC |

The graders were asked to evaluate each sample A, B and C using a pain scale ranging from 0 to 10, where 0 corresponds to no pain and 10 corresponds to the pain upon removal of the reference sample R.

The pain values for each sample A, B, and C were obtained as a mean of 24 observations.

The results collected from the test were analyzed by a statistical analysis program "Comparison of Population Means—Paired Samples", that showed that the differences between the pain values of the samples A, B, and C are statistically significant.

FLEXIBILITY TEST

The Flexibility Test is utilized to quantify the flexibility or stiffness in machine direction of the combination comprising the substrate and the topical adhesive applied thereon. The flexibility test used herein is a dynamic stiffness measurement (force to deform vs. distance deformed), that determines the average force (in grams) required to compress a substrate in machine direction.

Sample Preparation.

The test is performed on rectangular samples 60×20 mm of the selected material cut with the longer side oriented in machine direction, and provided on one surface with a continuous layer of the topical adhesive having a basis weight of 1350 g/m$^2$, applied with an Acumeter Model LH-1 extruder. Any protective release paper, if present, is removed before the test is carried on.

Apparatus.

1) Climatically controlled Lab. Maintenance of 23° C. and 50% Relative humidity.

2) Instron Limited, UK Model 6021 Dynamometer. Interfaced to a standard IBM computer with RS232 interface for Data logging. Data are sent to the computer in the form of distance and force values, and are read into a standard Microsoft Excel worksheet for analysis. The Instron is set to run a Compression test.

Load cell=10 N

Initial clamp separation=50 mm

Final clamp separation=15 mm

Distance sample to be deformed=35 mm

Compression speed=100 mm/min

3) Scissors.

Flexibility measurement.

The sample is positioned vertically and symmetrically between the fixed and the moving clamp, with each clamp holding a portion of the sample 5 mm wide along the respective short edge, with the exposed adhesive surface facing the operator. Contact between the clamps and the topical adhesive on the sample is prevented by applying on the topical adhesive a small rectangular piece of release paper about 20×5 mm on each end portion of the sample intended to be held by the respective clamp. The sample is slightly biased in order to bend during compression with the convexity on the adhesive surface. The clamps are so positioned to start the compression (in product machine direction) from a distance of 50 mm. The sample is compressed over a distance of 35 mm to a final clamp separation of 15 mm. The instrument details are given above.

The Instron records the clamp separation (in mm) and the force exerted to achieve this separation and sends this data via an RS232 interface to an IBM computer equipped with Microsoft Excel worksheet. The force and the distance data are loaded into the Excel software and the average force measurements over the full 35 mm compression cycle is determined.

The measurements are performed and averaged on 5 samples of the same type to ensure a representative stiffness value to be determined for each sample under investigation.

The pain upon removal was evaluated according to the Removal Pain Grade Test for three different combinations represented by samples A, B, and C having different stiffness values determined with the Flexibility Test, each combination having a layer of the same topical adhesive applied thereon.

The topical adhesive is an oil based composition containing 10% by weight of Kraton G-1651, a Styrene/Ethylene-Butylene/Styrene block copolymer available from Shell Co., 49% by weight of Kaydol, a paraffinic mineral oil available from Witco Co., 40% by weight of Escorez 5300, a hydrogenated tackifying resin available from Exxon Co., 0.7% by weight of Magnesium Stearate, a co-gelifying agent for oil available from Carlo Erba S.p.A., and 0.3% by weight of Irganox 1010, an antioxidant available from Ciba-Geigy.

So finally the formulation had the following percent composition:

| | |
|---|---|
| Kraton G-1651 | 10.0% by weight |
| Kaydol | 49.0% by weight |
| Escorez 5300 | 40.0% by weight |
| Magnesium Stearate | 0.7% by weight |
| Irganox 1010 | 0.3% by weight |

The composition has the following rheological properties at 37° C.

a) Elastic Modulus at 1 rad/s, $G'_{37}$=7038 Pa b) Viscous Modulus at 1 rad/s, $G''_{37}$=487 Pa c) Ratio of Elastic and Viscous Modulus at 1 rad/s, $G'_{37}/G''_{37}$=14.45 d) Ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})} = 1.11$$

e) The ratio of $\Delta G'_{37}$ over $G'_{37}$ (1 rad/s) was 0.291, with $\Delta G'_{37}$=2051 Pa.

The composition further has a viscous modulus $G''_{25}$ at 25° C. and at about 100 rad/sec of 4431 Pa.

The three substrates of the combinations A, B, and C are as follows:

Substrate of combination A is a nonwoven sold by Suominen under the trade name of Fibrella, code F2200/50, with a basis weight of 50 g/m$^2$.

Substrate of combination B is a polyester film 23 μm thick, such as that sold by Effegidi S.p.A. of Colorno (Parma, Italy).

Substrate of combination C is prepared by applying to a polyester film of the same type already described for substrate of combination B a medical double sided adhesive tape produced by Minnesota Mining and Manufacturing Company under the trade name of No. 1524 Medical Tape. Only one of the two layers of adhesive of the medical tape is exposed and used for attachment of the double tape to the polyester in order to form a composite layered substrate. The release paper of the second adhesive layer of the medical tape is kept in its position. The topical adhesive is applied onto the polyester surface of the composite substrate to form the combination C.

The stiffness of the three combinations and the respective pain grades are shown in the following table:

| Combination | Stiffness (g) | Pain grade |
|---|---|---|
| A | 3.26 | 5.52 |
| B | 11.42 | 4.78 |
| C | 32.53 | 3.65 |

The results show that for a given topical adhesive composition, represented by the value of $G''_{25}$ (100 rad/sec) of 4431 Pa, increasing stiffness values for the combinations of the substrates with the layer of topical adhesive correspond to reduced pain grades upon removal of the topical adhesive from the skin Of course the stiffness values for combinations of substrates with a topical adhesive used for attachment to the skin of disposable absorbent articles can be varied according to the empirical equations of the present invention in order to achieve acceptable removal pain grades with different topical adhesive compositions, and therefore with different values of $G''_{25}$ (100 rad/sec), within limits that can be readily determined by the man skilled in the art. Usually, in the field of disposable absorbent articles, this limit should not exceed 300 g. The same is true for possible selection of preferred topical adhesive compositions having different values of $G''_{25}$ (100 rad/sec) to be applied to a substrate having a certain fixed stiffness in order to reduce the pain grade upon removal of the absorbent article form the skin. Possible preferred limits for $G''_{25}$ (100 rad/sec) of a topical adhesive composition are implicitly defined e.g. by the preferred rheological characteristics of the topical adhesive compositions.

The pain upon removal can be further decreased when in the combination of the present invention the topical adhesive is provided onto the substrate in a layer having a thickness C measured in millimetres (mm) such that the viscous modulus $G''_{25}$ (100 rad/sec) and the thickness C of the topical adhesive satisfy the following empirical equation:

$$G''_{25} \leq [(4.26+C).1605]Pa$$

and preferably the following empirical equation:

$$G''_{25} \leq [(1.53+C).1724]Pa$$

as described in the European Patent Application entitled "Adhesive for secure topical attachment to the skin and comfortable removal with low level of pain, particularly of absorbent articles", filed together with the present application, inventors Fabio Cinelli, Peter Coles, and Italo Corzani, corresponding to the U.S. application Ser. No. 09/331,691.

What is claimed is:

1. A combination of a substrate with a hydrophobic topical adhesive applied thereon, said adhesive comprising at least 80% by weight of hydrophobic components, said combination intended for attachment of a disposable absorbent article to the skin, said combination having a stiffness S measured in grams (g) according to the Flexibility Test herein, said topical adhesive having an elastic modulus at a temperature of 37° C. (100° F.), G'37, in the range of 3000 Pa to 10000 Pa, a viscous modulus at a temperature of 37° C. (100° F.), G''37, in the range of 300 Pa to 5000 Pa, a viscous modulus at a temperature of 25° C. (77° F.), $G''_{25}$, characterized in that said viscous modulus $G''_{25}$ (100 rad/sec) of said topical adhesive and said stiffness S of said substrate satisfy the following equation:

$$G''_{25} \leq [(163.8+S).50.9]Pa$$

and wherein the ratio

G'37 (100 rad/sec)-G"37 (100 rad/sec)

G"37 (1 rad/sec)-G"37 (1 rad/sec)

is in the range 1 to 1.8.

2. A combination according to claim 1 wherein said viscous modulus $G''_{25}$ (100 rad/sec) of said topical adhesive and said stiffness S of said substrate satisfy the following equation:

$$G''_{25} \leq [(82.2+S).51.4]Pa.$$

3. A combination according to claim 1, wherein said substrate is a disposable absorbent article, said disposable absorbent article comprising a liquid pervious topsheet, a liquid impervious backsheet joined to said topsheet, and an absorbent core positioned between said topsheet and said backsheet.

4. A combination according to claim 1, wherein said topical adhesive is provided onto said substrate in a continuous layer.

5. A disposable absorbent article wherein said article is a sanitary napkin or a pantiliner for topical adhesive attachment to the skin of a wearer, said article comprising a combination of a substrate with a topical adhesive according to claim 1 for said attachment to the skin.

6. A combination according to claim 1, wherein said article is a sanitary napkin or a pantiliner.

7. A combination according to claim 1, wherein alternatively either $G'_{37}$ (100 rad/sec)-$G'_{37}$ (1 rad/sec) is not greater than 5000 Pa; or the ratio $$\frac{G'_{37}(100\ rad/sec) - G'_{37}(1\ rad/sec)}{G'_{37}(1\ rad/sec)}$$

is not greater than 1.

8. A combination according to claim 1, wherein alternatively either $G'_{37}$ (100 rad/sec)-$G'_{37}$ (1 rad/sec) is not greater than 5000 Pa; or the ratio $$\frac{G'_{37}(100\ rad/sec) - G'_{37}(1\ rad/sec)}{G'_{37}(1\ rad/sec)}$$

is not greater than 0.8.

9. A combination according to claim 1, wherein said adhesive is selected to have
alternatively either $G'_{37}$ (100 rad/sec)-$G'_{37}$ (1 rad/sec) is not greater than 2000 Pa; or the ratio $$\frac{G'_{37}(100\ rad/sec) - G'_{37}(1\ rad/sec)}{G'_{37}(1\ rad/sec)}$$

is not greater than 1.

10. A combination according to claim 1, wherein said adhesive is selected to have
alternatively either $G'_{37}$ (100 rad/sec)-$G'_{37}$ (1 rad/sec) is not greater than 2000 Pa; or the ratio $$\frac{G'_{37}(100\ rad/sec) - G'_{37}(1\ rad/sec)}{G'_{37}(1\ rad/sec)}$$

is not greater than 0.8.

* * * * *